United States Patent

Mavliev et al.

[11] Patent Number: 5,903,338
[45] Date of Patent: May 11, 1999

[54] CONDENSATION NUCLEUS COUNTER USING MIXING AND COOLING

[75] Inventors: Rashid A. Mavliev, Chicago, Ill.; Craig A. Parsons, Louisville, Colo.

[73] Assignee: Particle Measuring Systems, Inc., Boulder, Colo.

[21] Appl. No.: 09/022,104

[22] Filed: Feb. 11, 1998

[51] Int. Cl.$^6$ .................................................. G01N 1/26
[52] U.S. Cl. ........................................... 356/37; 356/338
[58] Field of Search ...................................... 356/37, 338

[56] References Cited

U.S. PATENT DOCUMENTS

| | | | |
|---|---|---|---|
| 3,592,546 | 7/1971 | Gussman | 356/37 |
| 3,694,085 | 9/1972 | Rich | 356/37 |
| 3,806,248 | 4/1974 | Sinclair | 356/37 |
| 4,293,217 | 10/1981 | Bird, Jr. et al. | 356/37 |
| 4,449,816 | 5/1984 | Kohsaka et al. | 356/37 |
| 4,790,650 | 12/1988 | Keady | 356/37 |
| 4,950,073 | 8/1990 | Sommer | 356/37 |
| 5,011,281 | 4/1991 | Harris | 356/37 |
| 5,076,097 | 12/1991 | Zarrin et al. | 73/61.1 |
| 5,239,356 | 8/1993 | Hollander et al. | 356/37 |
| 5,247,842 | 9/1993 | Kaufman et al. | 356/37 |
| 5,519,490 | 5/1996 | Nakata et al. | 356/338 |

FOREIGN PATENT DOCUMENTS

WO 97/33155  9/1997  WIPO ........................... 21/53

OTHER PUBLICATIONS

Continuous Automated Measurement of the Soluble Fraction of Atmospheric Particulate Matter, written by Poruthoor K. Simon and Purnendu K. Dasgupta, Analytical Chemistry, vol. 67, No. 1, Jan. 1, 1995, pp. 71–78.

Microphysical Measurements of Fog Formed in a Turbulent Jet, written by Madeleine L. Strum and Herbert L. Toor; Aerosol Science and Technology 16, 1992, pp. 151–165.

*Primary Examiner*—Robert H. Kim
*Assistant Examiner*—Zandra V. Smith
*Attorney, Agent, or Firm*—Duft, Graziano and Forest, PC

[57] ABSTRACT

A modified mixing-type condensation nuclei counter for measuring the size and number of small particles is presented. A gas stream is saturated with respect to a working fluid. The saturated gas at a first temperature is mixed in a growth chamber with a sample gas at a second temperature that is lower than the first temperature. The mixture of the saturated gas and the sample gas at different temperatures results in supersaturation of the mixed gas with respect to the working fluid. Particles in the sample gas act as nucleation sites for condensation of the working fluid. The particles are thus grown to a larger size and therefore are more easily measured by known light-scattering particle detection methods. The efficiency of the supersaturation process is made even more efficient by cooling the growth chamber to a third temperature which is lower than the second temperature or by turbulently mixing the saturated gas and the sample gas. False count rate is reduced by filtering the saturated gas before it is mixed with the sample gas to remove droplets of the working fluid from the saturated gas.

23 Claims, 4 Drawing Sheets

CONDENSATION NUCLEUS COUNTER USING MIXING AND COOLING

FIELD OF THE INVENTION

This invention relates to the field of particle detection. In particular, this invention relates to a condensation nucleus counter for particle detection that combines two streams at different temperature and cools the mixture to enlarge the size of the condensation nuclei to be measured.

STATEMENT OF THE PROBLEM

The long-term trend in the manufacture of semiconductor devices towards increasingly smaller device dimensions is expected to continue into the future, as evidenced by the predictions of the Semiconductor Industry Association's (SIA) National Technology Roadmap for Semiconductors (June, 1996). As a direct result of the shrinking device dimensions, the critical defect size has also shrunk.

According to the SIA Roadmap, this critical defect size will fall below 0.1 micrometers by 1998 and be 0.03 micrometers in 10 years.

Laser-based light scattering has long been the favored approach for detecting and sizing contaminants in clean room environments and in process fluids (liquids and gasses) used in semiconductor manufacturing. For contaminants smaller than about 0.1 micrometers in diameter, further increases in sensitivity become difficult to achieve because of the fast fall-off of the light scattering signal in the Rayleigh scattering regime (particle diameter much smaller than the wavelength of light). Therefore, to keep pace with the demands of the semiconductor industry, new technology is required. One method for extending the sensitivity of particle sizing instruments is by first enlarging the particle via nucleation and condensational growth to an easily detectable size by conventional light-scattering techniques. This approach is the basis of instruments known as Condensation Nucleus Counters (CNC's).

In a CNC, a small particle is "grown" to a larger size by nucleation and condensation of vapor-phase molecules onto the particle. The resultant large particle can then be easily detected by a simple laser particle counter. The vapor-phase molecules are typically deposited in a gas stream by passing the gas stream over a pool of the molecule in liquid form (called the "working fluid"). If the vapor pressure of the working fluid in the gas stream is equal to the equilibrium vapor pressure for the working fluid at a given temperature, then the gas stream is said to be saturated with that fluid. If the vapor pressure of the working fluid in the gas stream can be made to exceed its equilibrium vapor pressure, then the gas stream is called supersaturated. Supersaturation is a non-equilibrium condition thus the gas stream will attempt to return to equilibrium by condensing some of the vapor out onto either a surface or a particle present in the gas stream. Thus, the operational essence of a CNC is the supersaturation of the particle-containing gas stream.

The initial deposition of the working fluid on a particle is called nucleation. Condensational growth will continue to enlarge the particle size following nucleation provided the particle is exposed to the same or higher saturation conditions. The sensitivity of a particle counter is defined as the particle size at which 50% of the particles are detected. The critical first step of nucleation determines the sensitivity of a CNC and is approximately governed by the Kelvin equation which gives the critical diameter of a fluid particle, $d^*$, that is in equilibrium with its vapor:

$$d^* = \frac{4\gamma M}{\rho RT(\ln S)} \quad \text{EQN. 1}$$

Where:
- $\gamma$ is the surface tension of the working fluid;
- $M$ is the molecular weight of the working fluid;
- $\rho$ is the density of the working fluid;
- $R$ is the gas constant;
- $T$ is the temperature; and
- $S$ is the supersaturation ratio (vapor pressure of the working fluid divided by the equilibrium vapor pressure of the working fluid). Therefore, all particles larger than $d^*$ will nucleate and continue to grow while particles smaller than $d^*$ will not. Thus the sensitivity of a CNC is controlled by the supersaturation value achieved in the gas stream containing the particles.

While recognized as providing the best sensitivities, CNC's haven't been used widely for cleanroom monitoring for several reasons. The working fluid, typically alcohol or glycerol, used by existing CNC's to enlarge the size of sample particles gets depleted and the units must be regularly refilled every few days to keep them operational. A larger reservoir can be provided but this causes storage problems as butanol, the most common working fluid used in existing CNC's, is flammable and therefore has restrictions on its storage. In addition, the fluid is continuously exhausted during operation of the CNC and therefore raises human health and safety concerns. For CNC's using a chemically inert fluorinated working fluid (such as FC-43 by 3M) the cost of the fluid becomes prohibitive. Another disadvantage of most existing CNC's is their relatively low sampling rate of about 0.1 cubic feet per minute (cfm). A lower sampling rate means that accrual of a statistically significant number of particle counts requires more measurement time. A further problem with existing CNC's is that the presence of the fluid compromises the ruggedness of the instrument compared to non-CNC light-scattering particle counters. If the CNC unit is tipped or shaken during transport, the fluid may drip onto the optics and require extensive maintenance to dry before it can be used. CNC's are often used on mobile carts where an instrument prone to fluid contamination is a concern. A further problem with CNC's involves achieving a sufficiently low "false count rate". Ideally, the only detected particles flowing through a particle detection system are the particles of interest. Counts observed from a particle counter when no sample particles are present constitute the false count rate of the instrument. Since this represents the lowest concentration that can be measured by an instrument, the false count level is important for instruments intended to be used in ultra-clean environments as found in the semiconductor industry. False counts may originate from electrical noise in the detection electronics or from real particles generated internal to the instruments. False count rate reduction in CNC's can be challenging due to the presence of the working fluid which can itself be the source of vapor particles. This problem is expected to be worse at higher flow rates and when using higher vapor pressure working fluids (such as water).

There are two basic types of existing CNC's: mixing and cooling. Cooling-type CNC's achieve supersaturation by cooling a previously-saturated particle-containing sample stream. For a cooling-type CNC, supersaturation is determined by the relative temperatures of the incoming sample flow and the temperature it is being cooled to, the growth chamber temperature. Examples of cooling-type CNC's are found in U.S. Pat. No. 3,806,246 issued to Sinclair on Apr. 23, 1974 and U.S. Pat. No. 4,790,650 issued to Keady on Dec. 13, 1988. Mixing-type CNC's achieve supersaturation of the particle-containing sample stream by mixing a warm, saturated gas stream with a cooler gas stream. In a mixing-type CNC, supersaturation is created by the mixing of a warm saturated flow with a cooler particle-laden sample flow. The temperature of this mixed flow ($T_{mix}$) is the flowrate-weighted temperature average of these two flows. The supersaturation ratio is simply the total amount of vapor in the mixed flow (typically dominated by the contribution from the warm saturated flow), divided by the equilibrium amount of fluid expected under these conditions, which is just the vapor pressure of the fluid at temperature $T_{mix}$. Examples of mixing-type CNC's are found in U.S. Pat. No. 3,694,085 issued to Rich on Sep. 26, 1972 and U.S. Pat. No. 4,449,816 issued to Kousaka et al. on May 22, 1984. Most of the existing, commercial CNC's are cooling-type CNC's and most use a working fluid other than water.

There exists a need for a CNC having an increased sampling flowrate. There exists a further need for a CNC that uses a fluid that is readily available, can be plumbed to the instrument to provide maintenance-free operation, poses no health or safety concerns and is inexpensive. There further exists a need for a CNC that can be transported throughout a user's site without significant risk of damaging the operability of the CNC due to the operating fluid contacting the optics or other sensitive portions of the CNC.

Statement of the Solution

The Modified-Mixing-Type CNC (MMCNC) of the present invention solves the above problems and others thereby advancing the state of the particle detection art. The MMCNC achieves supersaturation of the sample stream through a combination of mixing two gas streams at different temperatures and by cooling the mixed stream. High flow rates are achieved as are low false count rates, even when water is used as the working fluid. The MMCNC is less susceptible to operational problems due to tipping of the device or spilling of the working fluid.

The MMCNC of the present invention is comprised of a saturator chamber, a saturator filter and a growth chamber. A gas stream runs through the saturator chamber and exits the saturator chamber as a saturated stream. The saturated stream is filtered through the saturator filter and then enters the growth chamber. The particles to be measured are carried in a sample stream which enters the growth chamber at a lower temperature than the saturated stream. The two gas streams, the saturated gas and the sample gas, are mixed in a growth chamber to produce supersaturation of the sample gas having particles entrained therein.

The saturated gas is filtered by the saturation filter to remove any particles from the saturated gas. This minimizes the extent to which the saturator chamber adds to the false count rate of the device. The MMCNC of the present invention is effective enough at reducing the false count rate that flow rates substantially above 0.1 cfm have been achieved and water, despite its high vapor pressure, can be used as the working fluid. In one embodiment of the MMCNC, the saturation filter is itself heated to maintain a temperature at least as warm as the saturator chamber. The filtered, saturated gas is mixed in the growth chamber with the sample gas.

Mixing of the two gas streams is enhanced, in one embodiment, by turbulently mixing the two streams. The mixing of the warm saturated gas with the cooler sample gas produces supersaturation of the mixed gas stream.

In a further embodiment of the present invention, the interior walls of the growth chamber are cooled to enhance the supersaturation of the sample gas. This embodiment combines the effects of existing mixing-type CNC's with the effects of cooling-type CNC's to produce a CNC having improved ability to grow particles for optical sensing.

One embodiment of the present invention employs a saturator chamber utilizing an impregnated fluoro-polymer material known as Nafion that is manufactured in tube form by Perma Pure, Inc. Nafion has the property of allowing certain fluids to pass and containing all others. Polar molecules such as water and alcohols diffuse through the Nafion material while most other substances including, for example, air and nitrogen cannot penetrate the Nafion material. One saturator chamber design uses thin-walled tubes formed of Nafion material which hold the working fluid of the CNC. The gas to be saturated is passed along the outside of the Nafion tubes. While the gas stream is in contact with the liquid-containing tubes in the interior of the saturator chamber, the gas stream is saturated by diffusion of the liquid molecules through the tubes and into the gas stream. This saturator design ensures that there is no direct liquid to gas contact thereby avoiding the contribution of liquid particles which add to the false count rate of the device. In addition, the CNC of the present invention is more robust with respect to movement of the device since the working fluid cannot directly contact the optical surfaces downstream.

In all of the embodiments of the present invention, particles in the sample gas operate as nucleation sites for condensation of the working fluid to grow the particles to a larger size. Well known light-scattering techniques are used to detect the grown particles.

DETAILED DESCRIPTION

Figure 1:
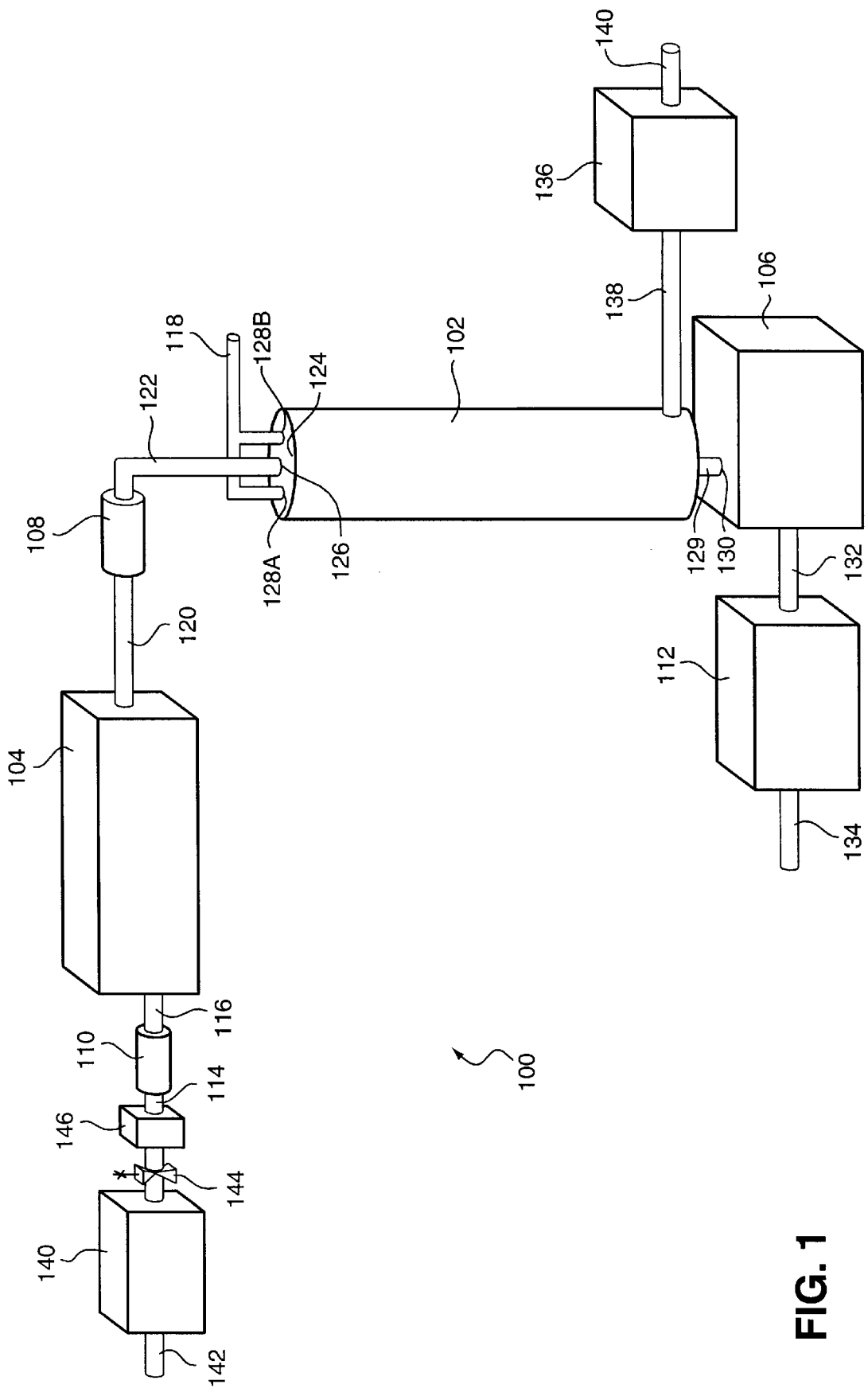
FIG. 1 depicts a block diagram of the MMCNC of the present invention.

Operation of MMCNC In General—FIG. 1

The MMCNC of the present invention solves the problems of the prior art thereby advancing the state of the particle detection art. The MMCNC achieves supersaturation of the sample stream through a combination of mixing two gas streams at different temperatures and by cooling the mixed stream. High flow rates are achieved as are low background counts, even when water is used as the working fluid. The MMCNC is also less susceptible to operational problems due to tipping of the device or spilling of the working fluid.

MMCNC 100 of the present invention is comprised of saturator chamber 104, saturator filter 108 and growth chamber 102. A gas stream runs through saturator chamber 104 and exits saturator chamber 104 as a saturated gas stream. The saturated gas stream is filtered through saturator filter 108 and then enters growth chamber 102. The particles to be measured are carried in a sample gas stream which enters growth chamber 102 through sample gas inlet 118 at a lower temperature than the saturated gas stream. The two gas streams, the saturated gas and the sample gas, are mixed in growth chamber 102 to produce supersaturation of the mixed gas with respect to the working fluid. Particles in the sample gas operate as nucleation sites for condensation of the working fluid to grow the particles to a larger size. The grown particles are drawn from growth chamber 102 to light scattering particle detection system 106 where well known light-scattering techniques are used to detect the size and number of grown particles.

Operation of MMCNC 100 is now described in more detail. A gas stream is drawn from an environment through inlet 142 by pump 140. Pump 140 draws about 0.07 cubic feet per minute of gas from the environment into MMCNC 100. An example of such a pump is a model MPU860 Diaphragm pump manufactured by KNF Neuberger. The gas flow through pump 140 is controlled by flow control valve 144 which opens and closes as appropriate to maintain the desired flow rate of gas through pump 140. The operation of flow control valve 144 is determined by a control signal from flow measuring device 146. In one embodiment of the present invention, flow measuring device 146 is an orifice plate across which the pressure drop is measured. The gas stream passes through pre-filter 110 and enters saturator chamber 104 through saturator inlet 116. As described in more detail with respect to FIGS. 2–3, the gas stream is saturated with a working fluid as it passes through saturator chamber 104. Saturator chamber 104 is heated to a temperature $T_1$ to aid the saturation process within saturator chamber 104.

The appropriate range for temperature $T_1$ depends upon the working fluid used in MMCNC 100. A range of temperature $T_1$ when water is the working fluid is 50–90° C., although temperatures outside this range could also be used within appropriate changes in flow rates, mixing conditions, or growth chamber temperature. A saturated gas stream exits saturator chamber 104 into conduit 120.

Figure 6:
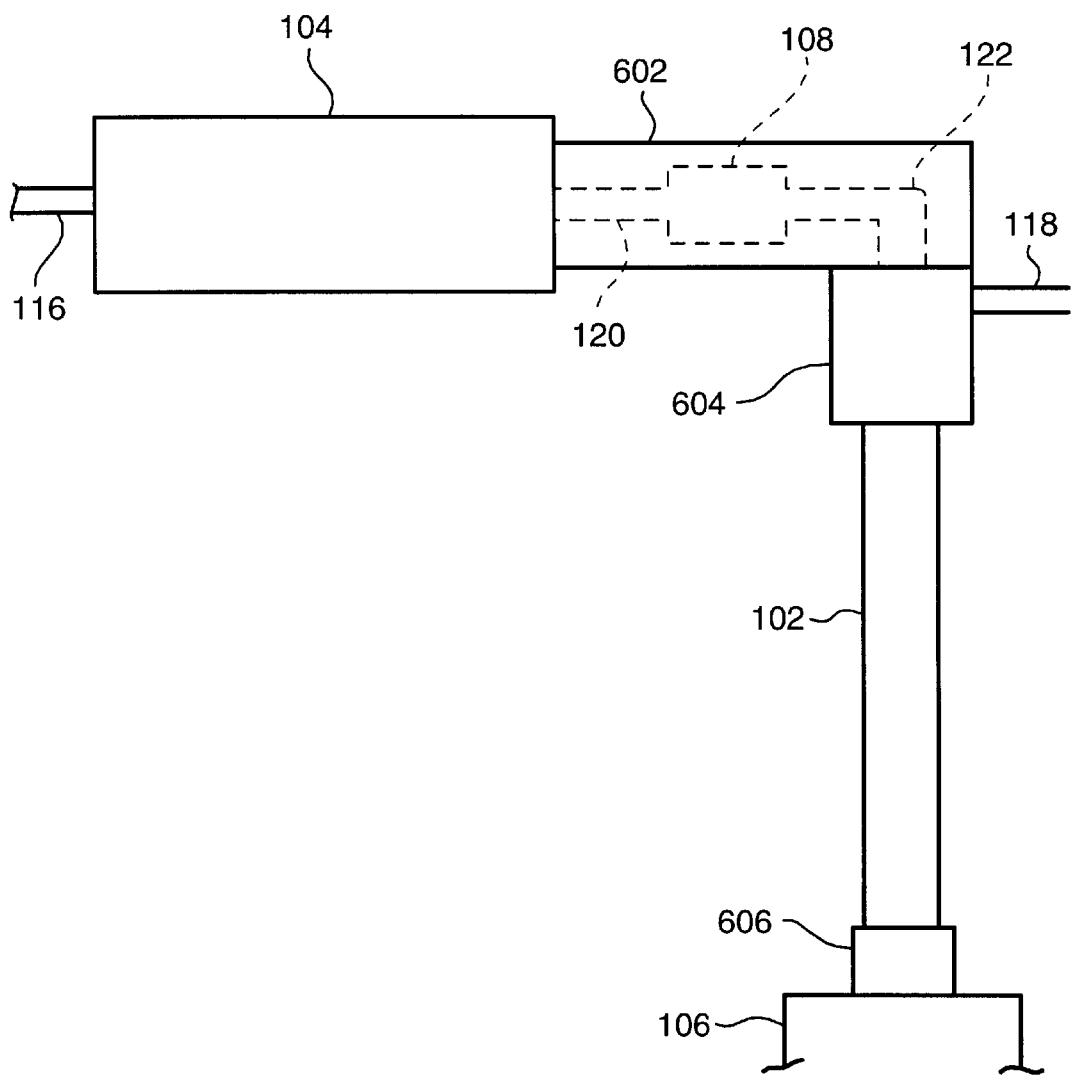
FIG. 6 depicts a block diagram of a portion of one embodiment of the MMCNC of the present invention.

The saturated gas stream passes through conduit 120 to saturator filter 108. In a preferred embodiment, saturator filter 108 is contained within the same housing as saturator chamber 104, as shown in FIG. 6. Saturator filter 108 is heated to a temperature $T_2$ that is no less, and is typically 5–15° C. greater than, temperature $T_1$. The heating of saturator filter 108 prevents vapor in the saturated gas stream from condensing in saturator filter 108. The saturated gas stream passes from saturator filter 108 to conduit 122.

Inlet end 124 of growth chamber 102 includes inlet 126 through which conduit 122 connects to growth chamber 102. A sample gas containing particles to be sensed enters sample gas inlet 118 from a process line (not shown) or environment (not shown). The sample gas is at a temperature $T_3$ which is less than temperature $T_1$ and is typically near room temperature (20° C.). For most choices of working fluid, the sample gas would be completely unsaturated with that fluid. However, when water is the working fluid, an uncontrolled amount of saturation (humidity) may be present when the sample gas is air. This variation in sample gas humidity would manifest itself as a small change in the achieved supersaturation level of the mixed and cooled gas stream in the growth chamber, and thus, affect the sensitivity of the instrument slightly. Typically, for operation in a cleanroom, air humidity is tightly regulated and the instrument could be calibrated under the same humidity conditions and operate at a constant sensitivity. For environments where air humidity isn't controlled, and the accompanying small variation in sensitivity isn't acceptable, the sample air could be pre-humidified or dried to a constant humidity level using, for example, the same techniques as discussed below in generating the saturated flow stream. Note that in this circumstance, the sample stream does not have to be 100% saturated; it's saturation level merely has to be kept at a constant value.

The sample gas enters growth chamber 102 through inlets 128A–B at inlet end 124 of growth chamber 102. The operation of growth chamber 102 is described in more detail with respect to FIG. 5. In general, the mixing of the saturated gas stream at a relatively high temperature and a sample gas at a relatively low temperature results in the supersaturation of the gas mixture. The particles entrained in the sample gas act as nucleation sites for condensation. The working fluid condenses on the particles and the particles are thereby grown from the size of the actual particle itself to the larger size of the grown particle. The grown particles exit growth chamber 102 through conduit 129 and pass through inlet 130 into light-scattering particle detection system 106.

Light-scattering particle detection system 106 is located proximal to growth chamber 102 so as to avoid the condensation of vapor on the connecting flow path walls between growth chamber 102 and light-scattering particle detection system 106 and to minimize particle loss to walls before they are counted by particle detection system 106. Light-scattering particle detection system 106 is a well-known device to those skilled in the art of particle detection systems. Suitable devices which could be used as light-scattering particle detection system 106 include a modified version of Model LPSC-310 laser particle counter manufactured by Particle Measuring Systems, Inc. The standard Model LPSC-310 laser particle counter is calibrated for a 1.0 cfm sample flow rate. For use in MMCNC 100, the laser particle counter is calibrated for a sample flow rate of 0.25 cfm. The number of grown particles is detected within light-scattering particle detection system 106.

The total air flow which exits light-scattering particle detection system 106 is determined by a "critical orifice" (not shown) to which conduit 132 is connected.

Those skilled in the art of CNC's recognize that there are many other methods to achieve flow control as well. The critical orifice is an orifice of diameter such that a constant flow is achieved when a vacuum of less than 0.53 times atmospheric pressure is applied to the downstream side of the critical orifice. In one embodiment of the present invention, the critical orifice diameter is 0.041 inches, the saturated gas flow rate, through pump 140, is 0.07 cfm and the sample gas flow rate, through inlet 118, is 0.25 cfm. Vacuum pump 112 provides the necessary vacuum and is well-known to those skilled in the art. Although a vacuum pump is shown in this embodiment, any pressure or vacuum producing device that creates a pressure differential between the inlets 142, 118 and outlet 134 can be used. One example of a suitable, commercially available vacuum pump is Gast Model 2032–V103. The saturated and particle-laden gas stream is drawn through light-scattering particle detection system 106, through conduit 132 to vacuum pump 112 and is exhausted through exhaust 134. Exhaust 134 may be connected to a process line (not shown) or exhaust 134 may operate to exhaust the gas stream into the environment.

Figure 5:
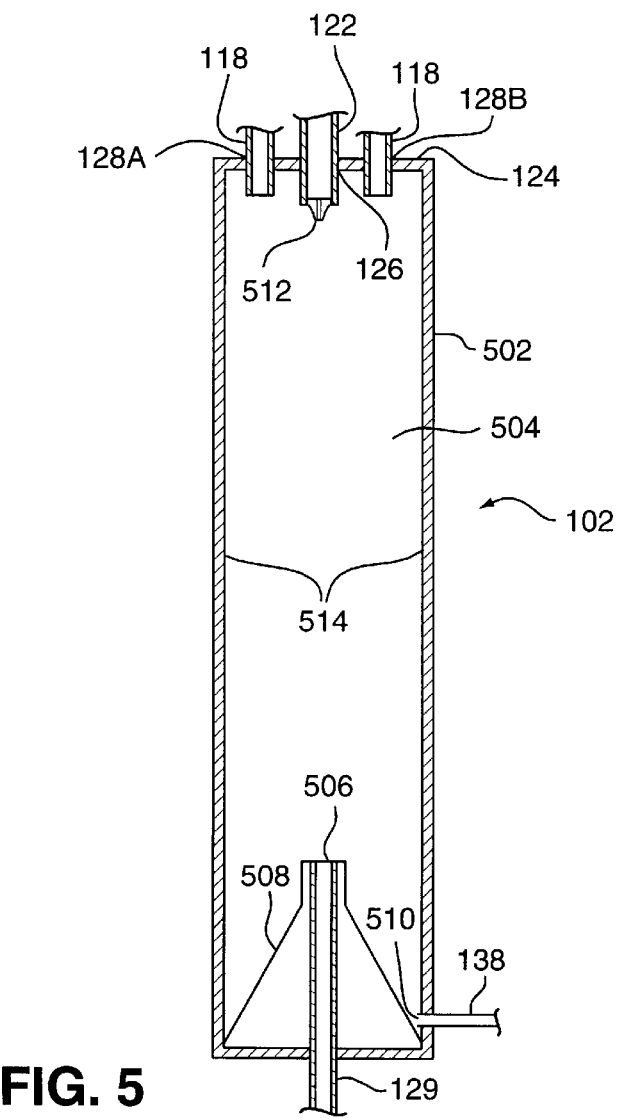
FIG. 5 depicts a drain plug design utilized in a growth chamber of the present invention.

As discussed herein with respect to FIG. 5, working fluid vapor condenses on the inner walls of growth chamber 102. This condensed fluid runs down the inner walls of growth chamber 102 and is pumped from growth chamber 102 by water pump 136 through conduit 138. Conduit 140 is connected to a waste-water collection system (not shown) or is connected to saturator chamber 104 (connection not shown) to re-circulate the working fluid.

Saturator Filter—FIG. 1

As noted above, saturator filter 108 removes particles from the saturated gas stream that would otherwise contribute to the false count rate of MMCNC 100. Saturator filter 108 also prevents working fluid from traveling from saturator 104 optics in light-scattering particle detection system 106 in the event of tipping of MMCNC 100. Saturator filter 108 is shown separately from saturator chamber 104 although it could alternatively be incorporated into the same structure or housing as saturator chamber 104, as shown in FIG. 6. Saturator filter 108 is maintained at temperature $T_2$ which is no less than temperature $T_1$ of saturator chamber 104. Preferably, saturator filter 108 is a sintered metal filter such as used for high-purity gas lines. Its all metal construction lends itself to being maintained at a known and controlled temperature $T_2$ so as to prevent the vapor in the gas stream from condensing. An example of such a filter is the Gas Shield Penta Filter manufactured by Mott Corporation. Those skilled in the art recognize that other types of filters would work as well in MMCNC 100.

Pre-filter 110 is not necessary to operation of MMCNC 100. Pre-filter 110 is less expensive than saturator filter 108, is easily replaced and is used to extend the life of saturator filter 108. An example of such a filter is the Ultipor filter by Pall.

As noted above, saturator filter 108 may be incorporated into the same structure as saturator chamber 104. FIG. 6 depicts a preferred embodiment of the present invention where saturator filter 108 is contained within filter housing 602 which is itself connected to saturator chamber 104. Also contained within filter housing 602 are conduits 120 and 122. Thus, the saturated gas passing through filter 108 and conduits 120 and 122 is maintained at temperature $T_2$ until it passes into growth chamber 102. It is advantageous to keep conduits 120 and 122 to as short a length as practicable to reduce the likelihood of the working fluid condensing within conduits 120 and 122.

Thermally insulating connector 604 thermally separates the "hot side" (saturator chamber 104 and saturator filter 108) from the cold side (growth chamber 102) of MMCNC 100. Connector 604 essentially envelopes inlet 118 and inlet end 124 of growth chamber 102. A material such as Ultem is used for thermally insulating connector 604 due to its high-temperature properties. Insulator 606 insulates the cold growth chamber 102 from the room-temperature light-scattering particle detection system 106. Since this connector doesn't contact the high temperature surfaces, a less expensive material, such as Delrin is used to form insulator 606.

Figure 2:
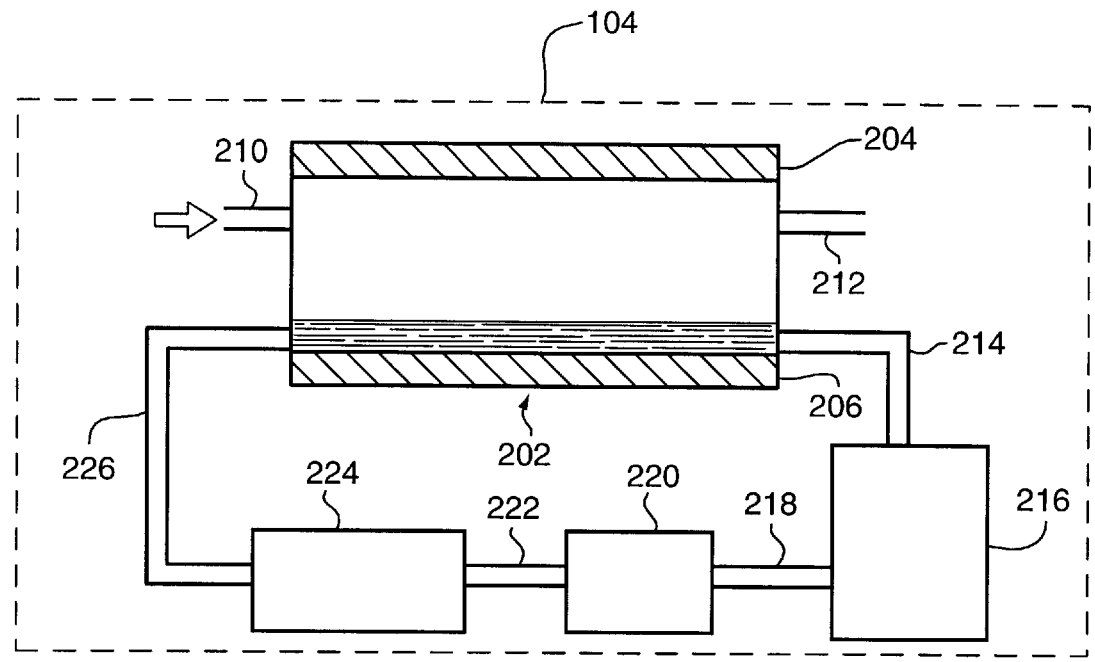
FIG. 2 depicts an embodiment of a saturator chamber utilized in the present invention.
Figure 3:
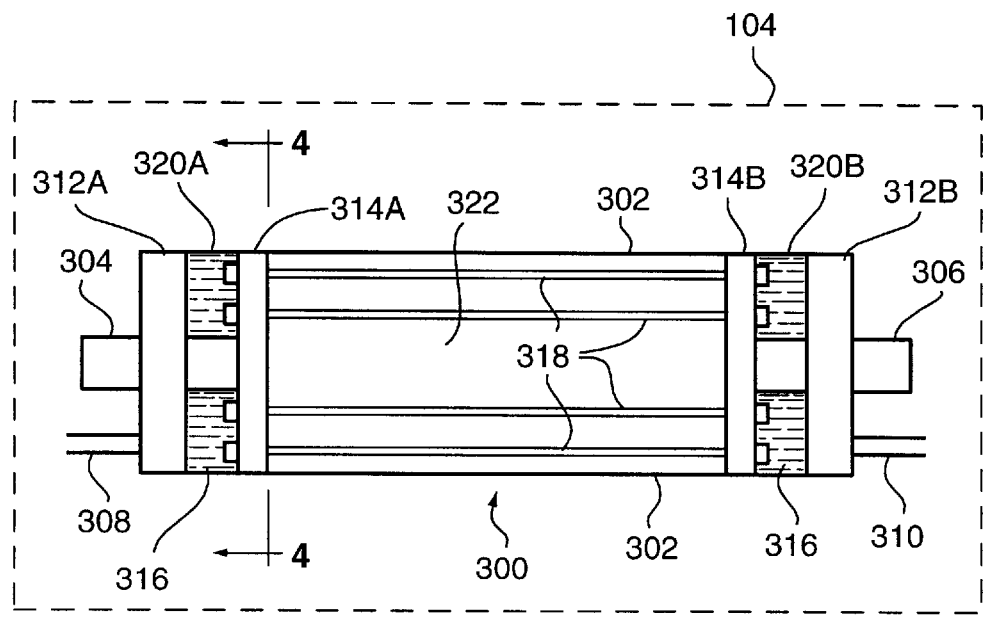
FIG. 3 depicts a further embodiment of a saturator chamber utilized in the present invention.
Figure 4:
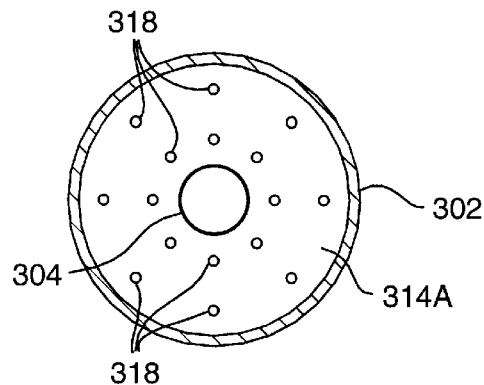
FIG. 4 depicts a cross-section of a growth chamber according to the present invention.

Saturator Chamber—FIGS. 2–4

FIG. 2 depicts a cross-section of one embodiment of saturator 104 used in MMCNC 100. Chamber 202 includes upper and lower walls 204 and 206, inlet 210 and outlet 212. A pool of working fluid 208 is maintained in the bottom of chamber 202. Walls 204 and 206 are heated to temperature $T_1$. by a heating element (not shown). The gas stream enters inlet 210, passes over working fluid 208, and exits through outlet 212. The gas stream is heated and saturated with respect to working fluid 208 as it passes through chamber 202. Recirculation pump 220 maintains the circulation of working fluid 208 through conduit 214 to reservoir 216, from reservoir 216 through conduit 218 to recirculation pump 220 and from recirculation pump 220 through conduit 222 through recirculation filter 224 and back to chamber 202 through conduit 226. In this way a constant volume of working fluid is maintained within chamber 202. In addition, the working fluid is continuously cleaned as it passes through recirculation filter 224. Chamber 202 may also be lined with a porous material such as polyvinyl alcohol sponge (not shown) in order to wick the working fluid to the entire interior surface of chamber 202 thereby improving the efficiency of the saturation process.

Those skilled in the art of CNC's recognize that there are a number of methods one can use to saturate a gas stream. Another approach would simply be to use a static pool of working fluid. Essentially, this idea could be implemented using just chamber 202 without the associated elements for recirculating the working fluid. Another saturator design is depicted in FIGS. 3–4.

FIGS. 3–4 depict a cross-section of a further embodiment of saturator 104 used in MMCNC 100. The gas stream enters saturator 300 through inlet 304 and exits through outlet 306 to, for example, saturator filter 108 of FIG. 1. The working fluid 316 enters saturator 300 through fluid inlet 308, passes through multiple tubes 318 and exits through outlet 310. Chamber 320A, which fills with working fluid 316, is formed by case end 312A and wall 314A. Likewise, chamber 320B, which fills with working fluid 316, is formed by case end 312B and wall 314B. Chambers 320A–B are sealed so that working fluid 316 cannot pass from chambers 320A–B into the interior chamber 322 and come into direct contact with the gas stream passing through saturator 300. Tubes 318 are formed from a material having the property of allowing certain materials to pass through the material while containing all others. An example of such a material is Nafion manufactured into tube form by Perma Pure Corporation. A fluid that can penetrate Nafion, water for example, is used as working fluid 316. Working fluid 316, maintained at temperature $T_1$, passes through Nafion tubes 318 by operation of a recirculation system such as shown as part of the saturator chamber 202 depicted in FIG. 3–4. The gas stream comes into contact with the Nafion tubes 318 and is thereby saturated with the working fluid which passes through the walls of the Nafion tubes. Nafion tubes 318 are preferably arranged circularly symmetric around interior chamber 322. There is no direct gas to working fluid contact in the saturator design of FIGS. 3–4. This ensures that working fluid particles do not add to the background count of the MMCNC.

Those skilled in the art of CNCs recognize that there are a number of means by which one can heat the saturator chamber. In one embodiment of the present invention, cartridge-type electrical heaters are inserted into the saturator chamber. FireRod electrical heaters manufactured by Watlow are an example of this type of heater.

Growth Chamber—FIG. 5

FIG. 5 illustrates a vertical cross-section view through growth chamber 102 of FIG. 1. Inlet end 124 of growth chamber 102 has inlets 128A–B through which gas inlet 118 extends to the interior 504 of growth chamber 102. Conduit 122, through which the saturated gas enters growth chamber 102, extends to the interior 504 of growth chamber 102. The sample gas enters interior 504 through gas inlets 128A–B and the saturated gas enters interior 504 through inlet 126. The two gases mix together in interior 504. Although only two inlets 128A–B are shown in FIGS. 1 and 5, any number of one or more inlets could be selected. It is preferable to use at least two inlets as this aids in the mixing of the two gas streams within interior 504.

Nucleation and condensational growth of the entrained particles entering through inlets 128A–B requires supersaturation of the gas mixture with respect to the working fluid.

Supersaturation is achieved by mixing of the warmer saturated gas with the cooler sample gas. Supersaturation is also achieved by cooling of the gas mixture as it traverses the growth chamber. In addition to creating higher supersaturation, cooling of the growth chamber lowers the absolute amount of working fluid vapor in the gas stream. This reduces the amount of working fluid condensation which occurs in pumps and pump lines beyond the instrument which could impair the operation of the pump. In a preferred embodiment of the present invention, mixing and cooling are both employed within growth chamber 102 to achieve higher supersaturation. Control of the supersaturation ratio for MMCNC 100, and thus the sensitivity of MMCNC 100, is obtained through control of temperatures $T_1$, $T_2$ and $T_3$, and the saturated and sample flow rates and saturation levels.

Interior surfaces 514 of walls 502 are cooled, as known to those skilled in the art of cooling-type CNC's, by a cooling device, not shown. Cooling of the growth chamber may be achieved by using thermo-electric devices (TED). TED are electrical solid-state devices such as the model CPI.4-127-045L manufactured by Melcor. Suitable heat sinks are required on one side of a TED to dissipate heat drawn from the cold side of the TED, as known to those skilled in the use of TED's. Other cooling means are also possible such as recirculating a refrigerant fluid, cooled to the desired temperature, around growth chamber 102. To achieve a uniform temperature in growth chamber 102, it is preferably constructed from a high thermal conductivity material such as copper. To prevent reaction with the working fluid, the copper growth tube may be coated with a more inert material such as nickel. Mixing of the saturated gas and the sample gas is enhanced by turbulently mixing the two gas streams. Turbulence also helps offset the difficulty expected in trying to create supersaturation in a gas stream via conductive-cooling for a working fluid with a high molecular diffusivity such as water. Supersaturation in a laminar-flow conductive-cooling scheme (as are all the commercially-available cooled CNC's) is favored by the thermal diffusivity of the gas stream being larger than the molecular diffusivity of the working fluid for which supersaturation is being generated. Turbulent flow makes the achieved supersaturation more dependent on the turbulent flow structure itself, rather than on the molecular and thermal diffusivities. Turbulent flow is created by sizing nozzle 512 of conduit 122, through which the saturated stream enters interior 504, such that the diameter of nozzle 512 results in a turbulent Reynolds number for the saturated gas as it enters growth chamber 102. Using the example of a saturated gas flow rate of 0.07 cfm, a nozzle 512 of 0.1 cm diameter results in a Reynolds number of 2800. Generally, Reynolds numbers of less than 2200 are laminar for cylindrical pipe flow. Non-laminar flow past a nozzle likely occurs at even lower Reynolds numbers. As the gas mixture moves from inlet end 124 of growth chamber 102 to and through outlet 506 of conduit 130, the entrained particles act as nucleation sites for condensation due to the state of supersaturation within growth chamber 102. The grown particles pass through outlet 506 and conduit 130 which, as depicted in FIG. 1, directs the grown particles directly into light-scattering particle detection system 106.

In addition to condensation of the working fluid on the particles entrained in the gas mixture, the working fluid also condenses on the interior surfaces 514 of walls 502 of growth chamber 102. The condensed working fluid moves downward along interior surfaces 514 under the force of gravity. To prevent the formation of large water droplets on the interior surfaces 514 of growth chamber 102, interior surfaces 514 may be roughened, e.g., by sandblasting, to encourage the condensed water to wet the surface more uniformly and thus prevent the formation of large droplets which could produce smaller vapor droplets by shedding into the gas stream. Guide 508 is formed to collect working fluid as it drains down interior surfaces 514 and direct the collected working fluid to conduit 138. Conduit 138, as described with respect to FIG. 1, is connected to fluid pump 136. Fluid pump 136 operates to pump the collected working fluid through outlet 510. The working fluid is then disposed of or recirculated to saturator chamber 104.

Control of the saturator chamber temperature ($T_1$), saturator filter temperature ($T_2$) and growth chamber temperature ($T_3$) is accomplished using well-known Proportional, Integral, Derivative (PID) controllers. For example, in a preferred embodiment of the present invention, a PID controller from Omega is used to control each of the three temperatures in MMCNC 100. As is known to those skilled in the art of PID controllers, the user sets a temperature setpoint for each temperature and the PID controller outputs a control signal that controls the operation of the heating or cooling device as appropriate to maintain the setpoint temperature. Those skilled in the art of CNCs will recognize there are other temperature control methods which may also be used.

Although specific embodiments are disclosed herein, it is expected that persons skilled in the art can and will design alternative particle measuring systems that are within the scope of the following claims either literally or under the Doctrine of Equivalents.

I claim:

1. A condensation nuclei counter comprising:
   a saturator chamber maintained at a first temperature and containing a working fluid such that a gas flowed through said saturator chamber becomes saturated with a vapor of said working fluid to form a saturated gas;
   a saturation filter, through which said saturated gas is conveyed, said filter maintained at a second temperature not less than said first temperature;
   a growth chamber for producing a supersaturation condition therein with respect to said working fluid, having a first inlet connected to an outlet of said saturation filter for receiving said saturated gas and a second inlet for receiving a sample gas at a temperature less than said first temperature, said sample gas having particles entrained therein upon which said working fluid condenses to produce enlarged particles;
   light scattering particle detection means for receiving said enlarged particles from said growth chamber and sensing a characteristic of said enlarged particles; and
   differential pressure means for causing said saturated gas and said sample gas to flow into said condensation nuclei counter.

2. The condensation nuclei counter of claim 1 wherein said saturator chamber comprises:
   a saturator pool which contains an amount of said working fluid and through which said gas flows;
   a reservoir of said working fluid from which said saturator pool is supplied with said liquid; and
   a pump for recirculating said working fluid from said reservoir through said saturator pool to maintain said amount of said working fluid in said pool.

3. The condensation nuclei counter of claim 2 wherein said saturator chamber further comprises:
   a re-circulation, filter through which said working fluid flows, connected as part of a re-circulation loop including said reservoir, said pump and said saturator pool.

4. The condensation nuclei counter of claim 3 wherein said re-circulation filter is connected in said recirculating loop so that said liquid flows through said re-circulation filter before reaching said saturator pool and after leaving said pump.

5. The condensation nuclei counter of claim 1 wherein said saturation filter removes particles from said saturated gas.

6. The condensation nuclei counter of claim 5 wherein said saturation filter comprises:
   a filtering means; and
   heating means for maintaining said filtering means at said second temperature.

7. The condensation nuclei counter of claim 1 wherein said saturator chamber comprises:
   heating means for maintaining said saturator chamber at said first temperature;
   a gas inlet through which said gas enters said saturator chamber on a first side of a membrane;
   a liquid inlet through which said working fluid enters said saturator chamber on a second side of said membrane; and
   said membrane allows said working fluid to pass from said second side to said first side thereby forming a vapor of said working fluid wherein said vapor contains substantially no particles from said liquid.

8. The condensation nuclei counter of claim 7 wherein said membrane is formed from a material that only allows polar molecules to diffuse through said membrane.

9. The condensation nuclei counter of claim 7 wherein said membrane is formed from Nafion.

10. The condensation nuclei counter of claim 7 wherein said membrane is formed in a tube through which said working fluid flows.

11. The condensation nuclei counter of claim 1 wherein said growth chamber further comprises:
    cooling means for maintaining inside walls of said growth chamber at said third temperature.

12. The condensation nuclei counter of claim 1 wherein said growth chamber further comprises:
    a nozzle through which said saturated gas enters said growth chamber such that said saturated gas has a non-laminar Reynolds number as it enters said growth chamber.

13. A condensation nuclei counter comprising:
    a saturator chamber maintained at a first temperature and containing a working fluid such that a gas flowing through said saturator chamber becomes saturated with respect to said working fluid to form a saturated gas;
    heating means for maintaining said saturator chamber at said first temperature;
    a growth chamber for producing a supersaturation condition therein with respect to said working fluid, having a first inlet connected to an outlet of said saturator chamber for receiving said saturated gas and a second inlet for receiving a sample gas at a temperature less than said first temperature, said sample gas having particles entrained therein upon which said working fluid condenses to produce enlarged particles;
    cooling means for cooling an interior of said growth chamber whereby a gas mixture of said saturated gas and said sample gas is cooled to a mixture temperature that is less than said first temperature;
    light scattering particle detection means for receiving said enlarged particles from said growth chamber and sensing a characteristic of said enlarged particles; and
    differential pressure means for causing said saturated gas and said sample gas to flow into said condensation nuclei counter.

14. The condensation nuclei counter of claim 13 wherein said saturator chamber comprises:
    heating means for maintaining said saturator chamber at said first temperature;
    a gas inlet through which said gas enters said saturator chamber on a first side of a membrane;
    a liquid inlet through which said working fluid enters said saturator chamber on a second side of said membrane; and
    said membrane allows said working fluid to pass from said second side to said first side thereby forming a vapor of said working fluid wherein said vapor contains substantially no particles from said liquid.

15. The condensation nuclei counter of claim 14 wherein said membrane is formed from a material that only allows polar molecules to diffuse through said membrane.

16. The condensation nuclei counter of claim 14 wherein said membrane is formed from Nafion.

17. The condensation nuclei counter of claim 14 wherein said membrane is formed in a tube through which said working fluid flows.

18. The condensation nuclei counter of claim 13 wherein said growth chamber further comprises:
    a nozzle through which said saturated gas enters said growth chamber such that said saturated gas has a non-laminar Reynolds number as it enters said growth chamber.

19. The condensation nuclei counter of claim 13 further comprising:
    a saturation filter, through which said saturated gas is conveyed, connected to an outlet of said saturator chamber and said first inlet of said growth chamber, said filter maintained at a second temperature not less than said first temperature.

20. The condensation nuclei counter of claim 19 wherein said saturation filter removes working fluid particles from said saturated gas.

21. The condensation nuclei counter of claim 20 wherein said saturation filter comprises:
    a filtering means; and
    heating means for maintaining said filtering means at said second temperature.

22. A method of operating a condensation nuclei counter for counting a number of particles, comprising the steps of:
    saturating a gas flow at a first temperature with a working fluid to produce a saturated gas flow;
    filtering said saturated gas flow to remove particles from said saturated gas flow;
    cooling a growth chamber within which said saturated gas and a sample gas having said particles entrained therein are mixed;
    growing a plurality of enlarged particles within said growth chamber using said particles as nucleation sites for condensation; and
    counting a number of enlarged particles with a light scattering particle detection means.

23. The method of claim 22 wherein said growing step includes:
    mixing in said growth chamber at a mixture temperature said saturated gas flow with said sample gas flow having said particles entrained therein, said mixture temperature being less than said first temperature thereby resulting in a condition of supersaturation within said growth chamber with respect to said working fluid.

* * * * *